United States Patent
Falowski

(10) Patent No.: US 12,121,729 B2
(45) Date of Patent: Oct. 22, 2024

(54) METHOD AND APPARATUS FOR INTRAOPERATIVE MONITORING OF LEAD PLACEMENT IN DORSAL ROOT GANGLION STIMULATION

(71) Applicant: Neural Integrative Solutions LLC, Santa Rosa, CA (US)

(72) Inventor: Steven M. Falowski, Coopersburg, PA (US)

(73) Assignee: Neural Integrative Solutions LLC, Santa Rosa, CA (US)

( * ) Notice: Subject to any disclaimer, the term of this patent is extended or adjusted under 35 U.S.C. 154(b) by 0 days.

(21) Appl. No.: 16/335,970

(22) PCT Filed: Sep. 25, 2017

(86) PCT No.: PCT/US2017/053296
§ 371 (c)(1),
(2) Date: Mar. 22, 2019

(87) PCT Pub. No.: WO2018/058057
PCT Pub. Date: Mar. 29, 2018

(65) Prior Publication Data
US 2019/0232062 A1    Aug. 1, 2019

Related U.S. Application Data

(60) Provisional application No. 62/398,809, filed on Sep. 23, 2016.

(51) Int. Cl.
*A61N 1/36* (2006.01)
*A61B 5/395* (2021.01)
*A61N 1/05* (2006.01)
*A61N 1/375* (2006.01)

(52) U.S. Cl.
CPC .......... *A61N 1/36135* (2013.01); *A61B 5/395* (2021.01); *A61N 1/0551* (2013.01); *A61N 1/36* (2013.01); *A61N 1/36128* (2013.01); *A61N 1/36175* (2013.01); *A61N 1/3752* (2013.01)

(58) Field of Classification Search
CPC ...... A61B 5/0488; A61N 1/0551; A61N 1/36; A61N 1/36128; A61N 1/36135; A61N 1/36175; A61N 1/3752
See application file for complete search history.

(56) References Cited

U.S. PATENT DOCUMENTS

| | | |
|---|---|---|
| 5,983,141 A | 11/1999 | Sluijter et al. |
| 7,177,690 B2 | 2/2007 | Woods et al. |
| 7,536,226 B2 | 5/2009 | Williams et al. |
| 2003/0199948 A1 | 10/2003 | Kokones et al. |
| 2004/0015211 A1 | 1/2004 | Nurmikko et al. |

(Continued)

OTHER PUBLICATIONS

International Search Report and Written Opinion dated Jan. 23, 2018 for corresponding PCT/US17/53296.

*Primary Examiner* — Jonathan T Kuo
*Assistant Examiner* — Vynn V Huh
(74) *Attorney, Agent, or Firm* — Sheridan Ross P.C.

(57) ABSTRACT

Disclosed and described here are an adapter for a neuromonitoring system for placement of an electrode in a subject and a method for confirming placement of an electrode on an appropriate nerve fiber of a dorsal root ganglion during a dorsal root ganglion stimulation procedure.

23 Claims, 7 Drawing Sheets

(56) References Cited

U.S. PATENT DOCUMENTS

| | | | |
|---|---|---|---|
| 2006/0052826 A1* | 3/2006 | Kim | A61N 1/36071 607/2 |
| 2006/0095090 A1* | 5/2006 | De Ridder | A61N 1/36036 607/57 |
| 2006/0276720 A1* | 12/2006 | McGinnis | A61B 5/0408 600/544 |
| 2006/0287678 A1* | 12/2006 | Shafer | A61N 1/36071 607/2 |
| 2009/0204119 A1* | 8/2009 | Bleich | A61B 17/320758 606/79 |
| 2010/0010334 A1* | 1/2010 | Bleich | A61B 17/1757 606/108 |
| 2012/0209346 A1* | 8/2012 | Bikson | A61N 1/36034 607/45 |
| 2014/0350636 A1 | 11/2014 | King et al. | |
| 2016/0339251 A1* | 11/2016 | Kent | A61N 1/36139 |

* cited by examiner

| | ○ | ○○ | ○○○ | ○○○○ |
|---|---|---|---|---|
| 1 | ORANGE | GRAY | YELLOW | WHITE |
| 2 | RED | PURPLE | WHITE/ PINK | WHITE/ GREEN |
| 3 | BROWN | BLUE | WHITE/ BROWN | WHITE/ YELLOW |
| 4 | BLACK | GREEN | WHITE/ BLACK | WHITE/ PEACH |

| | | | | | | | |
|---|---|---|---|---|---|---|---|
| ① | BLACK | ⑤ | YELLOW | ⑨ | GRAY | ⑬ | WHITE/PINK |
| ② | BROWN | ⑥ | GREEN | ⑩ | WHITE | ⑭ | WHITE/PEACH |
| ③ | RED | ⑦ | BLUE | ⑪ | WHITE/BLACK | ⑮ | WHITE/YELLOW |
| ④ | ORANGE | ⑧ | PURPLE | ⑫ | WHITE/BROWN | ⑯ | WHITE/GREEN |

METHOD AND APPARATUS FOR INTRAOPERATIVE MONITORING OF LEAD PLACEMENT IN DORSAL ROOT GANGLION STIMULATION

CROSS REFERENCE TO RELATED APPLICATIONS

This application claims the benefit of and priority to PCT/US2017/053296, filed on Sep. 25, 2017, entitled, "Method and Apparatus For Intraoperative Monitoring Of Lead Placement in Dorsal Root Ganglion Stimulation," which claims the benefit of and priority to U.S. Provisional Application No. 62/398,809, filed on Sep. 23, 2016, which are hereby incorporated by reference in their entirety into this application.

TECHNICAL FIELD

The present disclosure relates generally to Dorsal Root Ganglion (DRG) stimulation, and more particularly relates to an apparatus and method for neuromonitoring in DRG stimulation.

BACKGROUND

The DRG is a spinal structure that includes bundles of sensory cell bodies and plays a role in chronic neuropathic pain. Each spinal level has a corresponding DRG from a specific dermatome of the body. The anatomy and positioning of the DRG is consistent and reproducible. The size of the DRG increases as one moves from superior to inferior in the lumbar spine. In addition, the DRG moves more lateral in the foramen as you traverse lower in the spine. It is the most lateral at L5 vertebra. The dorsal aspect of the DRG is involved in sensory perception, while the ventral aspect of the DRG includes motor.

DRG stimulation has been shown to be an effective therapy in the treatment of chronic neuropathic pain and is presently used to treat regions of focal pain. It involves stimulation of the DRG at its junction between the peripheral nervous system and the central nervous system. The most common use in the United States is for the treatment of intractable pain in the lower limbs of those patients with the diagnosis of Complex Regional Pain Syndrome (CRPS) Type I and II, but is also used for the treatment of failed back surgery syndrome, postsurgical pain such as that following an inguinal hernia repair, and peripheral neuropathy.

During the DRG stimulation procedure, the placement of one or more leads is confirmed by an awake patient intraoperative testing to confirm adequate placement in the dorsal foramen with a sensory perception threshold. During intraoperative testing of the awake patient, paraesthesias are generated by stimulation of the DRG. Proper lead placement in the dorsal foramen is confirmed with the onset of paraesthesias prior to motor contractions. Awaking a patient from anesthesia and asking such patient to provide feedback regarding the various responses is challenging.

SUMMARY

In view of the foregoing, the inventor recognized a need for a method to confirm the lead placement in an asleep patient without awakening the patient for awake paraesthesia testing and addressed the shortcomings of the current state of the technology. Disclosed here are novel protocols and apparatuses for use in neuromonitoring during DRG stimulation lead placement in an asleep patient. The neuromonitoring protocol can be used in an asleep patient to assure proper positioning of the DRG electrode in the dorsal foramen by evaluating Somato-Sensory Evoked Potential (SSEP) responses in the absence of Electro-Myogram (EMG) responses.

Embodiments include systems for placement of an electrode in a subject. One such system includes an electrode contact operable to be implanted on a nerve fiber of a dorsal root ganglion of a subject; an adapter containing an electrode end operable to provide an electrical connection with the electrode contact and a plug end connected to a plug; the plug connecting the adapter to a neuromonitoring device; and the neuromonitoring device operable to provide a selective trigger of electrical stimulation via the adapter to the electrode contact when the electrode contact is implanted on the nerve fiber of the dorsal root ganglion and to record a response to the selective trigger of electrical stimulation. In certain embodiments, the neuromonitoring device includes a constant current stimulator. The selective trigger of electrical stimulation can include a pulse width ranging from 10 to 500 microseconds. In certain embodiments, the selective trigger of electrical stimulation can include a pulse width ranging from 200 to 500 microseconds. In certain embodiments, the selective trigger of electrical stimulation can include a pulse width ranging from 200 to 300 microseconds. The selective trigger of electrical stimulation can include a constant rate ranging from 1 to 500 Hz. In certain embodiments, the selective trigger of electrical stimulation can include a constant rate ranging from 1 to 100 Hz. In certain embodiments, the selective trigger of electrical stimulation can include a constant rate ranging from 10 to 50 Hz. In certain embodiments, the neuromonitoring device records a plurality of responses to the selective trigger of electrical stimulation. One of the plurality of responses can be a somatosensory evoked potential response to the selective trigger of electrical stimulation, or an electromyogram response to the selective trigger of electrical stimulation, or both. In certain embodiments, the plug end of the adaptor can contain a detachably connected plug. The plug can connect the adapter to the neuromonitoring device via a DIN connector.

Embodiments include methods for confirming placement of an electrode in a subject. One such method includes placing a stimulating electrode on a nerve fiber in proximity to a dorsal root ganglion; providing increasing amount of electrical stimulation to the nerve fiber via the stimulating electrode to elicit a somatosensory evoked potential response and an electro-myogram response; measuring the somatosensory evoked potential response and the electro-myogram response using a plurality of recording electrodes; decreasing amount of electrical stimulation to the nerve fiber until there is no detectable electro-myogram response; ensuring continued somatosensory evoked potential response; and determining correct placement of the stimulating electrode on a dorsal nerve fiber of the dorsal root ganglion when there is presence of a continued somatosensory evoked potential response in the absence of the detectable electro-myogram response. The method can also further include the step of determining incorrect placement of the stimulating electrode on a ventral nerve fiber of the dorsal root ganglion when there is no continued somatosensory evoked potential response in the absence of the detectable electro-myogram response; and repositioning the stimulating electrode on the nerve fiber of the dorsal root ganglion. These methods can be used with subjects under sedation. These methods can be used with subjects who are unable to provide verbal feedback. In certain methods, the step of placing a stimulating electrode on the nerve fiber of the dorsal root ganglion is guided by fluoroscopic imaging.

The stimulating electrode can be supplied with a selective trigger of electrical stimulation from a neuromonitoring device using an adaptor. In certain embodiments, the electromyogram response is measured using a recording electrode placed at a muscle group corresponding to a dermatomal level ranging throughout a spine. The dermatomal level can include one or more of a cervical, thoracic, or lumbar level. For example, the electro-myogram response is measured using a recording electrode placed in an adductor hallucis muscle and the stimulating electrode in a L5 dermatome. The electro-myogram response can be measured using a recording electrode placed in an iliopsoas muscle and the stimulating electrode in a L1 dermatome. The electro-myogram response can be measured using a recording electrode placed in an adductor brevis or longus muscle and the stimulating electrode in a L2 dermatome. The electro-myogram response can be measured using a recording electrode placed in a quadricep muscle and the stimulating electrode in a L3 or L4 dermatome. The electro-myogram response can be measured using a recording electrode placed in a gastrocnemius muscle and the stimulating electrode in a S1 dermatome.

BRIEF DESCRIPTION OF THE DRAWINGS

A better understanding of the present disclosure can be obtained when the following detailed description of the disclosed embodiments is considered in conjunction with the following drawings, in which.

DETAILED DESCRIPTION

Figure 1:
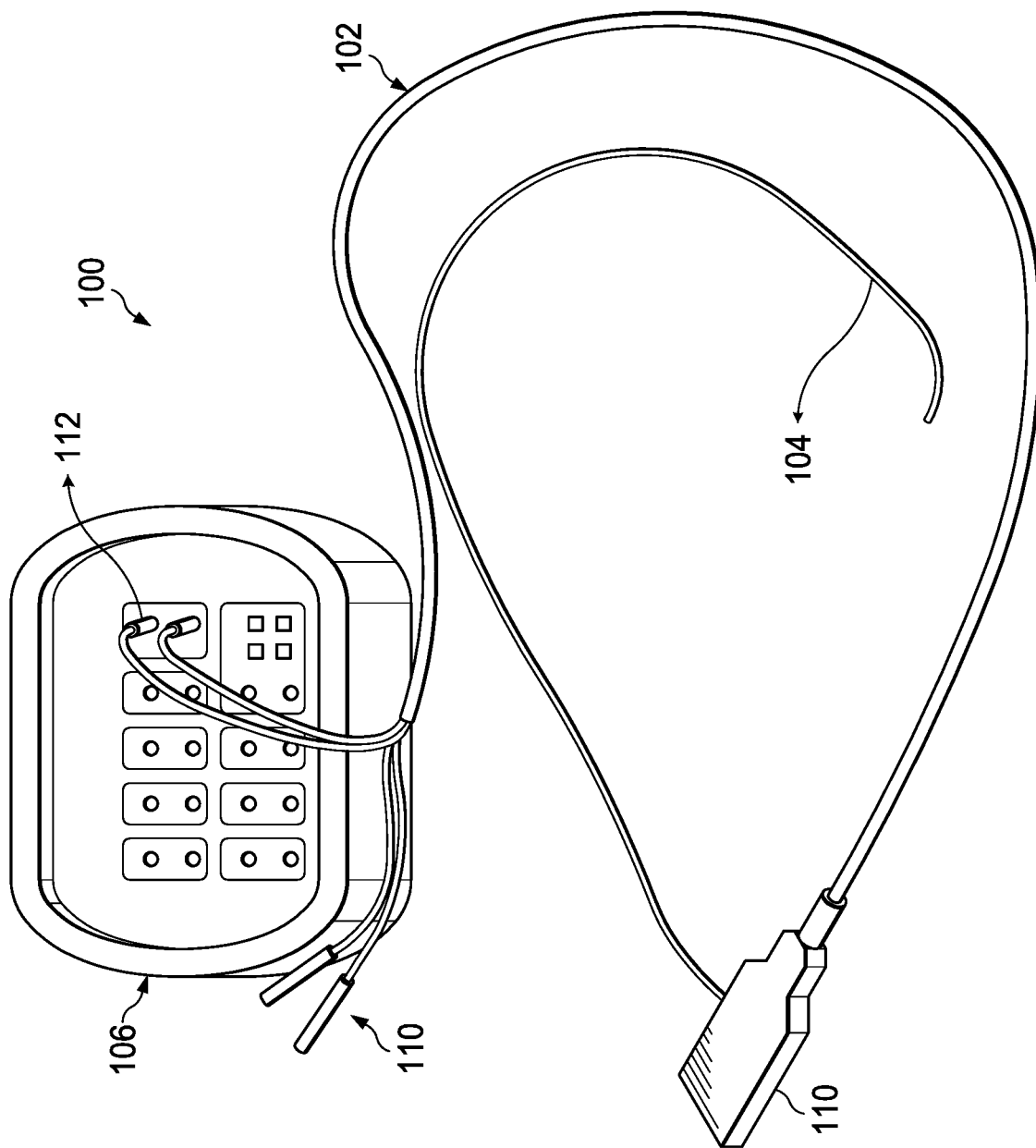
FIG. 1 is a diagrammatic representation of a system with a custom adapter, which connects an electrode to a constant-current stimulator, according to an exemplary embodiment.

Disclosed here are novel protocols and apparatuses for use in neuromonitoring during DRG stimulation lead placement in an asleep patient. The neuromonitoring protocol is used with an asleep patient to assure proper positioning of the DRG electrode in the dorsal foramen by generating SSEP responses in the absence of EMG responses. Intraoperative neuromonitoring is used to provide a ratio of sensory and motor thresholds whereby if the sensory (SSEP) thresholds are notably lower than the motor, then the lead is considered to be closer to the sensory aspect of the DRG and not too close to motor aspects of the DRG.

Embodiments include systems for placement of one or more electrode contacts in a subject. The system includes at least an electrode contact that is implanted on a nerve fiber of a dorsal root ganglion of a subject, and an adapter containing an electrode end operable to provide an electrical connection with the electrode contact and a plug end connected to a plug. In an embodiment, the electrical end of the adapter connects to the Abbott Axium DRG® system. The electrode end can be adopted to connect to any electrode suitable for this application. This plug connects the adapter to a neuromonitoring device. In an embodiment, the adapter is modified to connect with a DIN connection of a Cadwell® neuromonitoring device. The adaptor can be modified to contain any appropriate electrical end as required for connection to any neuromonitoring machine. This neuromonitoring device is used to both provide the trigger and also measure the response to the trigger. In an embodiment, the neuromonitoring device provides a selective trigger of electrical stimulation via the adapter to the electrode contact when the electrode contact is implanted on the nerve fiber of the dorsal root ganglion. It also records a response to the selective trigger of electrical stimulation using recording electrodes. The neuromonitoring device includes a constant current stimulator. The selective trigger of electrical stimulation includes a pulse width ranging from 10 to 500 microseconds. The selective trigger of electrical stimulation includes a constant rate ranging from 1 Hz to 500 Hz. The neuromonitoring device records a plurality of responses to the selective trigger of electrical stimulation. One of the plurality of responses is a somatosensory evoked potential response to the selective trigger of electrical stimulation. One of the plurality of responses is an electromyogram response to the selective trigger of electrical stimulation.

Embodiments include methods for confirming placement of an electrode in a subject. One such method includes placing a stimulating electrode on a nerve fiber in proximity to a dorsal root ganglion; providing increasing amount of electrical stimulation to the nerve fiber via the stimulating electrode to elicit a somatosensory evoked potential response and an electro-myogram response; measuring the somatosensory evoked potential response and the electro-myogram response using a plurality of recording electrodes; and decreasing amount of electrical stimulation to the nerve fiber until there is no detectable electro-myogram response while there is continued somatosensory evoked potential response. The correct placement of the stimulating electrode on a dorsal nerve fiber of the dorsal root ganglion is determined when there is presence of a continued somatosensory evoked potential response in the absence of the detectable electro-myogram response. There is incorrect placement of the stimulating electrode on a ventral nerve fiber of the dorsal root ganglion when there is no continued somatosensory evoked potential response in the absence of the detectable electro-myogram response; and one has to reposition the stimulating electrode on the nerve fiber of the dorsal root ganglion. This protocol can be implemented when subject is under sedation and does not require waking the subject to provide feedback. This protocol can be implemented when subject is unable to provide any verbal feedback. The initial placement of the stimulating electrode on the nerve fiber of the dorsal root ganglion can be guided by fluoroscopic imaging.

Performing the procedure using neuromonitoring differs from the traditional awake-patient technique in that the patient remains anesthetized throughout the procedure, and the accuracy of the placement and expected sensory and motor thresholds for stimulation are determined objectively using a combination of SSEP and spontaneous or free-run EMG (f-EMG) testing. The electrode is placed utilizing fluoroscopic imaging, and then the device is connected to the neuromonitoring system via a custom adapter, as shown in FIG. 1. This custom adapter is necessary to implement this protocol as the immediate recording of the responses require the ability of the neuromonitoring machine to control the trigger of stimulation through the electrode.

FIG. 1 is a diagrammatic representation of a system 100 with a custom adapter 102, which connects one or more electrodes 104 to a constant-current stimulator 106, according to an exemplary embodiment. The electrode contact 104 is supplied with electrical stimulation from the constant-current stimulator 106 that also runs the traditional SSEP modes. The custom adapter 102 contains a cable with internal wires. Each individual internal wire correlates with one contact on the electrode 104, and is subsequently connected to a plug 110 terminating with a DIN (Deutsches Institut fur Normung) connector. As used herein, a plug is a device for making an electrical connection, especially between an electrode contact and the electrical stimulation device, and containing an insulated casing with pins that fit into ports on the plug end of the adaptor and into appropriate slots on the electrical stimulation device. In an embodiment, the adapter 102 is connected via a DIN 42802 connector, which is a standard connection for the Cadwell® stimulation system, but can be altered to connect to any stimulation device. FIG. 1 shows two plugs 112 with DIN connectors, which correlate to the ability to control two contacts. In an embodiment, the cable is designed to connect to the St. Jude Medical Axium® Neurostimulator System intra-operative testing connector cables and box (connector cable MN11350), but the cable can be modified to connect to any electrode used in this regard.

Figure 2:
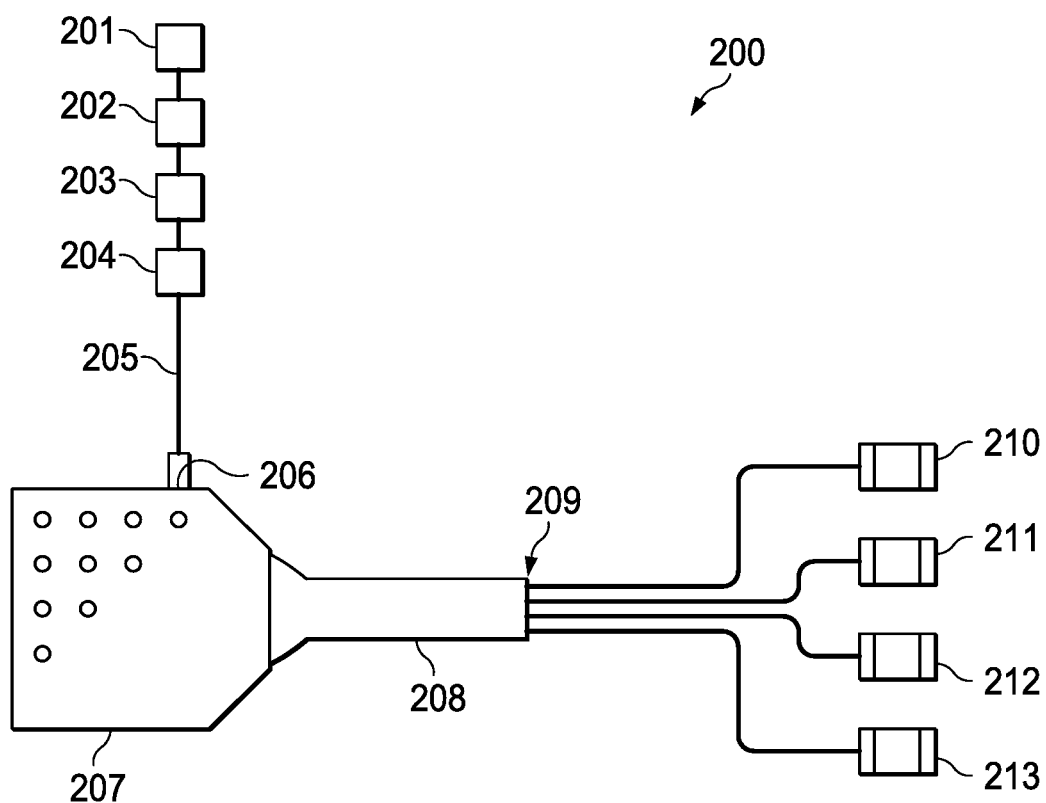
FIG. 2 is a diagrammatic representation of the DRG electrode/custom adapter with four contacts, according to an exemplary embodiment.

FIG. 2 is a diagrammatic representation of the DRG electrode/custom adapter 200 with four contacts 201, 202, 203, and 204, according to an exemplary embodiment. The four contacts 201, 202, 203, and 204 are spaced at predetermined intervals, and are intended to provide stimulation at the target DRG. These four contacts 201, 202, 203, and 204 are connected via a lead 205 to an electrode port 206 on the electrode end 207 of the custom adaptor 200. The electrode end 207 is connected via an extension cable 208 to the plug end 209 of the custom adaptor 200. The plug end 209 contains at least as many plugs 210, 211, 212, and 213 as the number of contacts 201, 202, 203, and 204, and each plug corresponds to a particular contact. In certain embodiments, the plugs 210, 211, 212, and 213 are part of the plug end 209 of the custom adaptor 200. In certain embodiments, the plugs can be detachably connected to the plug end 209 of the custom adaptor 200.

Figure 3:
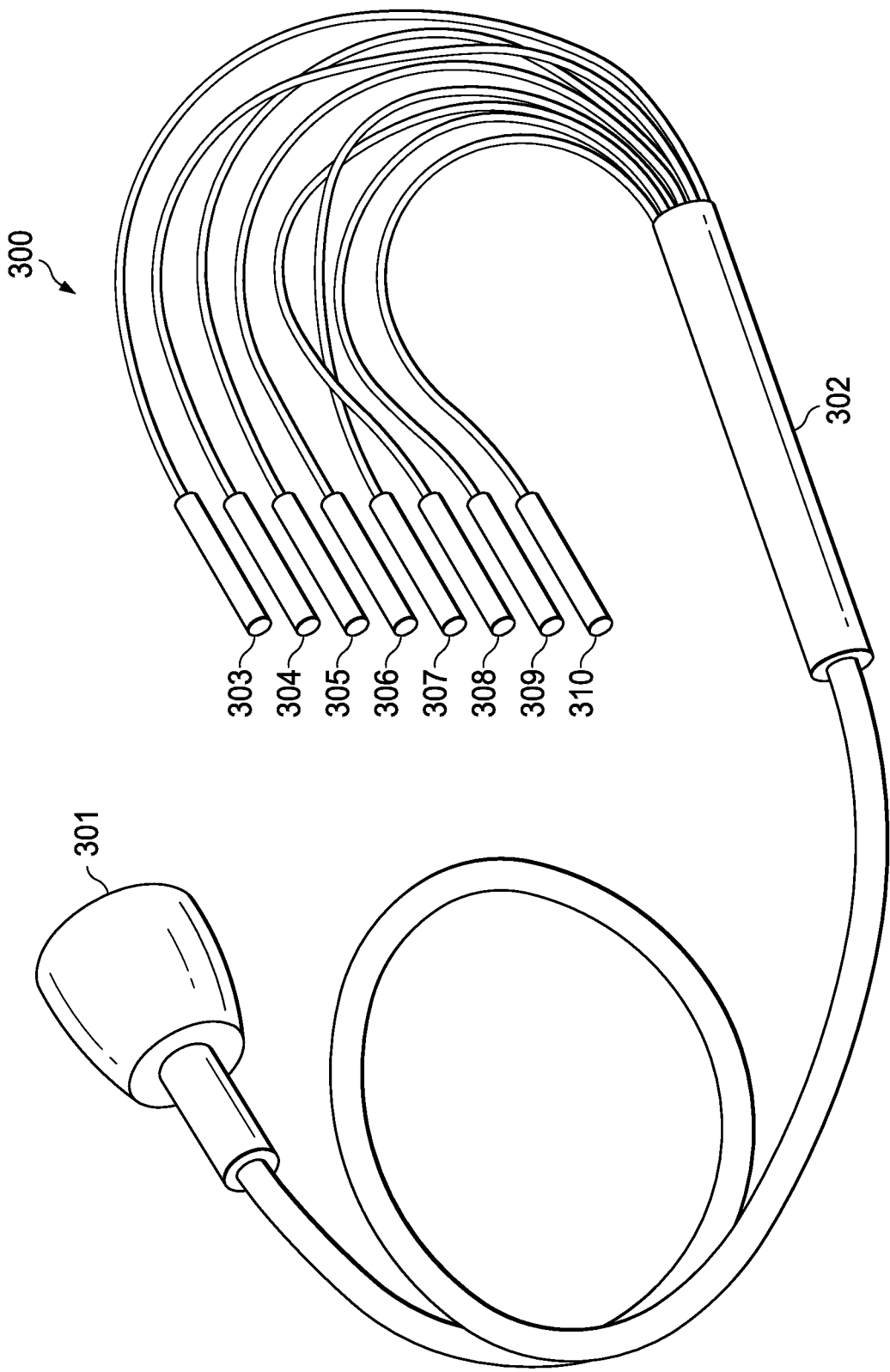
FIG. 3 is a diagrammatic representation of custom adapter, according to an exemplary embodiment.

FIG. 3 is a diagrammatic representation of custom adapter 300, according to an exemplary embodiment. In this embodiment, the custom adapter 300 has an electrode end 301 and a cable 302 that houses eight plugs 303, 304, 305, 306, 307, 308, 309, and 310. Each of the eight plugs correspond to an electrode contact that can be connected to the electrode port on the electrode end 301 of the custom adapter 300. Therefore, the eight plugs 303, 304, 305, 306, 307, 308, 309, and 310 with eight DIN connections correlate to the ability to control eight contacts, two electrodes with four contacts each.

Figures 4A, 4B:
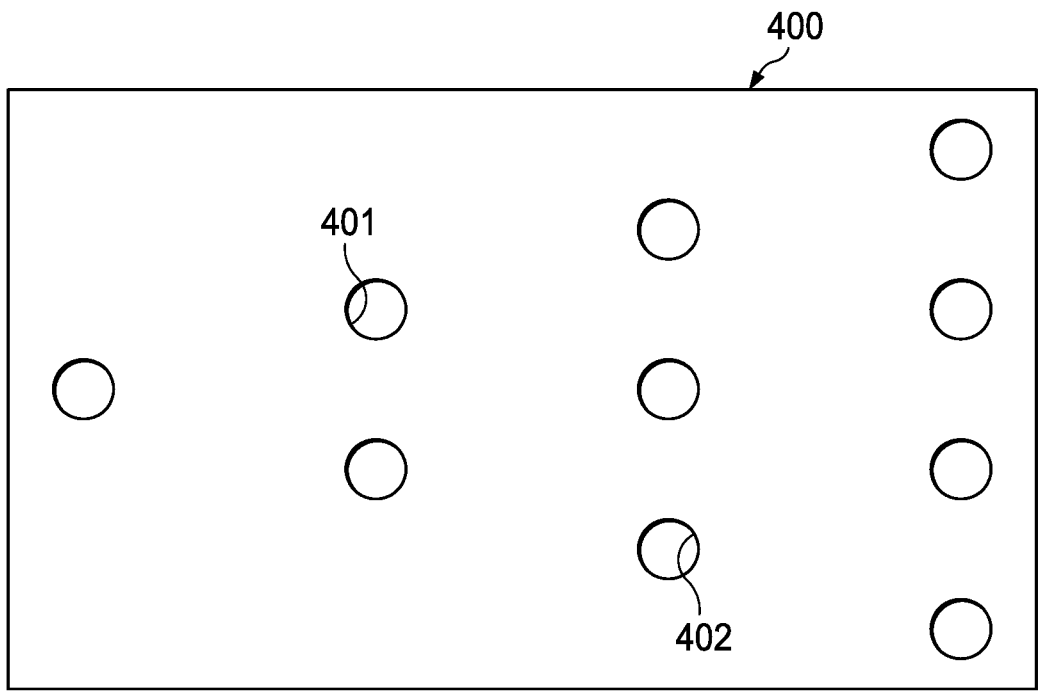
FIG. 4A is a diagrammatic representation of an electrode end of a custom adaptor with the internal wiring of a 16-contact setup, according to an exemplary embodiment.
FIG. 4B is a tabular representation of the color coded electrode contacts that can be connected to each of the electrode ports of the custom adaptor with the internal wiring of a 16 contact setup, according to the exemplary embodiment of FIG. 4A.
Figures 4C, 4D:
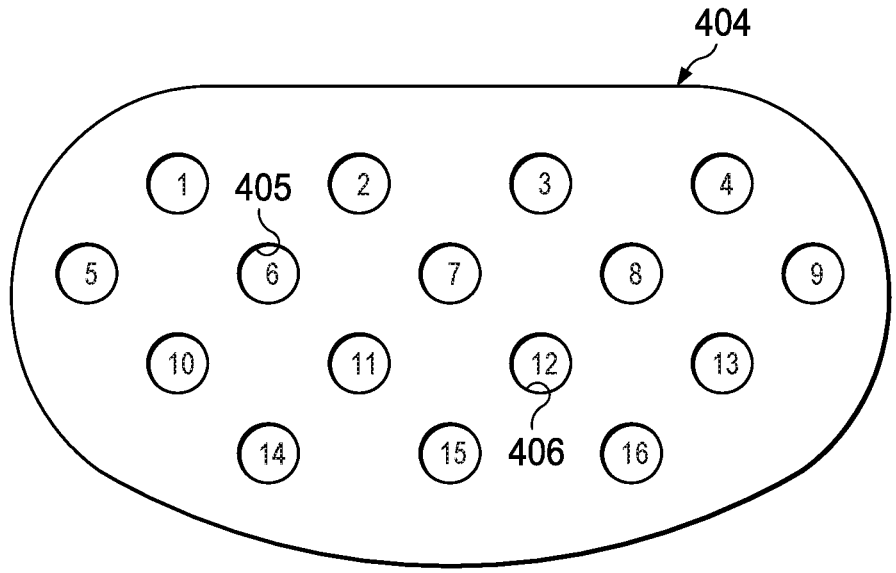
FIG. 4C is a diagrammatic representation of a plug end of a custom adaptor with the internal wiring of a 16-contact setup, according to an exemplary embodiment.
FIG. 4D is a tabular representation of the color coded plugs that can be connected via the plug end of FIG. 4C to each of the electrode contacts of the custom adaptor with the internal wiring of a 16-contact setup, according to an exemplary embodiment.

FIG. 4A is a diagrammatic representation of an electrode end 400 of a custom adaptor. This electrode end 400 has electrode ports, such as 401 and 402, that are configured to receive up to ten leads. FIG. 4B is a tabular representation of the color coded electrode contacts that can be connected to each of the electrode ports of the custom adaptor. For example, port 401 is configured to receive one of the electrode contacts that are coded gray, purple, blue, or green. For example, port 402 is configured to receive one of the electrode contacts that are coded yellow, white/pink, white/brown, or white/black. FIG. 4C is a diagrammatic representation of a plug end 404 of a custom adaptor. The plug end 404 has ports, such as 405 and 406, to receive up to sixteen plugs. In certain embodiments, the cable contains 16 internal wires that can control 16 contacts, which would be incorporated as 4 electrodes per lead. FIG. 4D is a tabular representation of the color coded plugs that can be connected to each of the electrode contacts of the custom adaptor. For example, port 405 is configured to receive the plug that is coded green, which would be receiving signals from the corresponding electrode contact that is also coded green. For example, port 406 is configured to receive the plug that is coded white/brown, which would be receiving signals from the corresponding electrode contact that is also coded white/brown.

In an embodiment, the custom adaptor is sold as part of a kit that contains one or more of the following: a neuromonitoring device, one or more leads which may be used in combination with a lead extension and the accessories and tools used for implanting the system.

While the invention has been described in detail above with reference to specific embodiments, it will be understood that modifications and alterations in the embodiments disclosed may be made by those practiced in the art without departing from the spirit and scope of the invention. All such modifications and alterations are intended to be covered. This adapter allows that DRG system to connect with a constant current stimulator such as the Cadwell system, but can be modified or altered to connect to other external stimulation systems.

As part of DRG stimulation, electrode contacts from one or more leads are placed on the DRG using a standard percutaneous technique for introduction of the lead into the epidural space. In an embodiment, a 4-contact electrode is placed inferior to the pedicle of the desired level on the dorsal aspect of the DRG in the foramen. In certain embodiments, targeted nerve root levels include the lower thoracic and lumbar-sacral levels. In other embodiments, targeted nerve root levels can include the cervical, upper thoracic, lumbar, and sacral levels, separately or in combination. The placement of each lead on the DRG requires confirmation of its position in the dorsal aspect of the foramen to ensure it is stimulating the sensory fibers. Ventral positioning leads to uncomfortable motor contractions without the desired effect of pain control.

Fluoroscopic imaging, in both an anterior-posterior and lateral projection, is generally utilized as a first step in placement confirmation. After proper placement of the DRG electrode under fluoroscopic imaging, further confirmation is generally performed by awake patient intra-operative testing to confirm adequate placement in the dorsal foramen with a sensory perception threshold. During intra-operative testing of the awake patient, paraesthesias are generated by stimulation of the DRG. Proper lead placement in the dorsal foramen is confirmed with the onset of paraesthesias prior to motor contractions. Awaking a patient from anesthesia and asking such patient to provide feedback regarding the various responses is challenging.

In an embodiment, the protocol for the use of neuromonitoring requires a constant current stimulator that controls the trigger point in which the stimulation is delivered. This is a required feature as the generated signal, whether SSEP or f-EMG, can only be recorded for less than a second afterward. The adapter disclosed and described in this disclosure allows for an electrode implanted in the body to be connected to the stimulation system so that the system can control that trigger. Given that DRG stimulation is of a single nerve root, embodiments of the system have these capabilities in order to run neuromonitoring to confirm placement in an asleep placement. The use of an external stimulator controlling the trigger for placement of spinal and DRG electrodes is novel, as well as the protocol designed around this technique. Embodiments include modifications and alterations to this protocol or adapter that controls the trigger. While this application refers to asleep patients, this term is intended to cover patients who are asleep as well as any patient who is not providing feedback regarding the stimulation. This may include patients who are mildly or heavily sedated as well as fully awake patients who refuse to, or are otherwise unwilling or incapable of providing feedback.

To perform the described neuromonitoring protocol, the disclosed system uses at least one of the many embodiments of the disclosed adapter. Certain benefits of the disclosed adapter include: (a) it allows access to control stimulation of each individual contact; (b) it gives the ability to connect to a stimulation system; and (c) it allows the user to control trigger point of stimulation. The selective trigger of electrical stimulation can include a pulse width ranging from 10 to 500 microseconds. In certain embodiments, the selective trigger of electrical stimulation can include a pulse width ranging from 200 to 500 microseconds. In certain embodiments, the selective trigger of electrical stimulation can include a pulse width ranging from 200 to 300 microseconds. The selective trigger of electrical stimulation can include a constant rate ranging from 1 to 500 Hz. In certain embodiments, the selective trigger of electrical stimulation can include a constant rate ranging from 1 to 100 Hz. In certain embodiments, the selective trigger of electrical stimulation can include a constant rate ranging from 10 to 50 Hz.

Alternate embodiments disclosed here include an adapter that has one or more connections. In an embodiment, the connection is a DIN connection. The number of DIN connections will often be between 1 and 16 but may be as many as 32, 64, 512, or greater. Some alternative embodiments may use any of a large array of known alternative connections other than a DIN connection. Alternative embodiments may use any connection that achieves the same benefits described above. In order to use a certain subset of connections, the choice of internal plugs is so adjusted that only the plugs required to control the contacts incorporated into each lead are utilized. Alternative embodiments may use known variations of contacts and lead electrodes as well. In particular, alternative embodiments may incorporate both percutaneous electrodes, paddle electrodes, surgical plate electrodes, cylindrical electrodes and/or any other implantable electrode.

Disclosed embodiments include a method of confirming placement of contacts using neuromonitoring techniques. Disclosed embodiments may be used for confirming contact placement in the spine between the lower thoracic and sacral levels. The disclosed embodiments may additionally and/or alternatively be used for the entire cervical, thoracic, lumbar, and/or sacral spine. Certain embodiments may be particularly beneficial when applied to the cervical spine due to the sensitive nature of the structures.

Monitoring for the surgery includes placing bilateral Ulnar and Posterior Tibial Nerve (PTN) SSEPs, and f-EMG for muscles that represent the appropriate nerve level(s) for the stimulator placements. In an embodiment, recording electrodes are placed in multiple muscles primarily supplied by the targeted nerve root level, as well as an additional muscle primarily supplied by a nerve root above the targeted nerve root, and one supplied by the level below the targeted nerve root, to allow for variations in an individual's nerve root level to the supplied muscles. Table 1 lists the muscles that are most commonly monitored; however additional muscles may be used for any of these levels.

TABLE 1

Typical Muscle Relationships to Nerve Root Levels

| Nerve Root Level | Representative Muscles |
| --- | --- |
| L1 | Iliopsoas |
| L2 | Adductor Brevis and Longus |
| L3 | Adductor Magnus, Quadriceps |
| L4 | Quadriceps |
| L5 | Tibialis Anterior, Adductor Hallucis |
| S1 | Gastrocnemius |

Figure 5A:
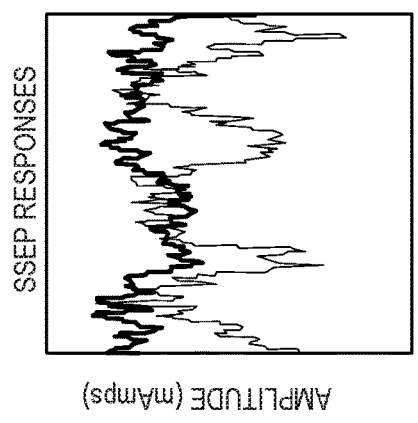
FIGS. 5A and 5B show SSEP and EMG responses in the Adductor Hallucis Muscle following electrical stimulation at L5 dermatome at 3.3 milliampere (mA), according to an exemplary embodiment.
Figure 5B:
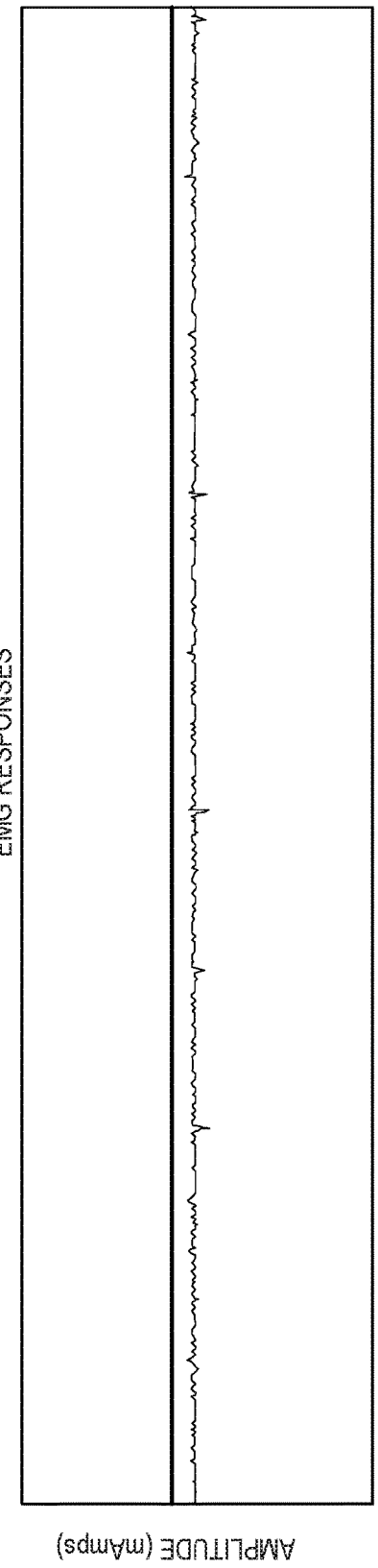
Figure 5C:
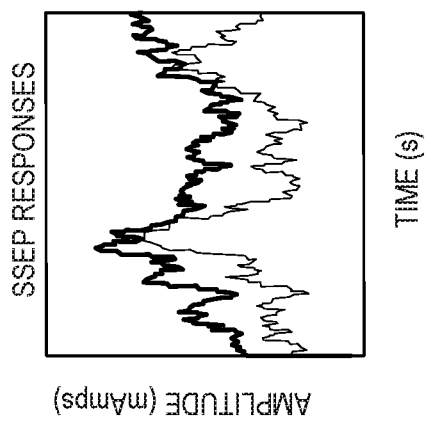
FIGS. 5C and 5D show SSEP and EMG responses in the Adductor Hallucis Muscle following electrical stimulation at L5 dermatome at 1.5 mA, according to an exemplary embodiment.
Figure 5D:
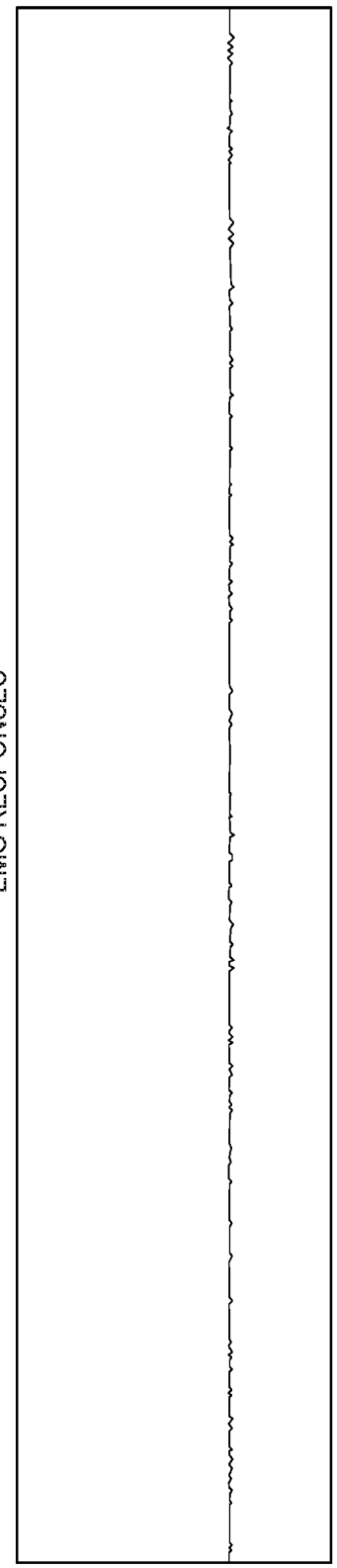

SSEPs and EMG are monitored as for any typical spine surgery. At the time of testing the stimulator electrode placement, regular SSEP testing is temporarily suspended, but f-EMG continues. The same-side PTN SSEP stimulator channel is switched to a low-current mode for better resolution in determining thresholds. The electric stimulation ranges from 0 mA to 5 mA. The SSEP trial is started and the stimulation current level is slowly raised from 0 mA until Compound Motor-unit Action Potential (CMAP) responses in the muscle(s) corresponding to the stimulated nerve root level are visualized; this is the motor threshold for the targeted DRG. If the stimulation level significantly exceeds the typical threshold level, different combinations of contacts and/or polarity conventions can be tried until the motor threshold is at an acceptable level. Once desired motor threshold is determined, the SSEP trial is stopped, cleared, restarted, allowed to run to completion, and stored. For that trial, a time marker is placed at the cortical trough or peak. Then, the SSEP is run at progressively lower levels than the motor threshold until the SSEP cortical peak disappears. The last stimulation level at which the cortical peak remains present is considered the sensory threshold. A sensory threshold that is equal to or even greater than the motor threshold indicates a potential ventral placement of the electrode and should prompt repositioning. FIGS. 5A and 5B show SSEP and EMG responses in the Adductor Hallucis Muscle following electrical stimulation at L5 dermatome at 3.3 milliampere (mA), according to an exemplary embodiment. FIGS. 5C and 5D show SSEP and EMG responses in the Adductor Hallucis Muscle following electrical stimulation at L5 dermatome at 1.5 mA, according to an exemplary embodiment. In comparing FIGS. 5B and 5D, the resolution of the EMG response is observed by noting the decrease of peaks and valleys in FIG. 5D as compared to FIG. 5B. There is no change in the SSEP response as shown by substantial similar recordings in FIGS. 5A and 5C. In each of the FIGS. 5A and 5C, the bold waveform is the baseline or reference SSEP response recording, and the second waveform is the newly generated response.

In addition to the entire spine, disclosed embodiments may be applied to peripheral nerves as opposed to the DRG. Disclosed embodiments will be equally useful in confirming contact placement for peripheral nerves as well as DRG and/or nerves of the central nervous system. Disclosed techniques may be useful for any procedure in which the trigger point of stimulation must be closely monitored and/or controlled by a medical professional.

Example

A study was conducted of 6 patients undergoing DRG stimulation surgery in a single institution performed by a single surgeon. The protocol and the results are also discussed in a non-patent publication, titled "A Prospective Analysis of Neuromonitoring for Confirmation of Lead Placement in Dorsal Root Ganglion Stimulation." by Steven M. Falowski and Andreas Dianna in the journal Operative Neurosurgery, and available at https://academic.oup.com/ons/article/4060569. The demographic information, diagnosis and lead placement for the patients is shown in Table 2.

TABLE 2

Patient Demographics, Diagnosis, and Lead Placement

| Patient | Age (years) | Sex | Diagnosis | Lead Placement |
|---|---|---|---|---|
| A | 51 | Male | Complex Regional Pain Syndrome | Left L5 |
| B | 21 | Male | Complex Regional Pain Syndrome | Left L3 and L4 |
| C | 43 | Male | Failed Back Surgery Syndrome, Complex Regional Pain Syndrome | Right L1 and L2 |
| D | 70 | Male | Peripheral Neuropathy | Bilateral L4 and L5 |
| E | 57 | Female | Complex Regional Pain Syndrome | Left L4 and L5 |
| F | 55 | Male | Peripheral Neuropathy | Bilateral L5 |

The 6 patients (A-F) ranged from 21 to 70 years of age, with 5 males and 1 female. Diagnoses of these 6 patients included CRPS, peripheral neuropathy, and failed back surgery syndrome. The case series included a total of 12 leads placed in the 6 patients involving L1-L5. Lead placement ranged from 1 lead (patient A) to 4 leads (patient D) per patient. Lead confirmation was confirmed by both awake intraoperative testing as well as asleep testing utilizing neuromonitoring. Patients were used as their own control.

Each patient underwent trial placement of leads, which were connected to tunneled extensions for a one week trial period. All patients had successful trials and were subsequently converted directly to permanent implant with removal of the extensions and connection to the generator. System implant included the Axium® Neurostimulator System (Spinal Modulation; LLC, Menlo Park, CA, a wholly owned subsidiary of St Jude Medical).

Placement of the trial leads were performed while under light sedation with Propofol. Fluoroscopic imaging was utilized for placement and confirmation within the foramen. Each patient was then awakened and test stimulation was given to determine sensory thresholds. Motor thresholds were also determined if possible. At this point the patient was placed back under sedation and neuromonitoring was then utilized for threshold determinations utilizing SSEP and f-EMG testing. Further analysis included a lead in which awake intraoperative testing returned low motor thresholds from ventral placement. This lead was also tested with neuromonitoring prior to being repositioned into the dorsal foramen.

Intraoperatively, the stimulation parameters remained consistent across awake and asleep testing. Pulse width (PW) ranged from 200-300 µs, while rate was maintained at 20 Hz. Contact configuration for testing was based on the position of the contacts within the foramen in which the two contacts below the pedicle were used in a bipole configuration. This was most commonly 2− (cathode) and 3+ (anode). However, contact configuration could be adjusted based on responses generated. Post-operative programming was also kept consistent for both PW and rate, but contact configuration was adjusted based on patient feedback.

In each patient, paraesthesias were generated prior to motor contractions in the awake patient. For each patient, SSEP responses were present after lowering below the dropout threshold of EMG responses with neuromonitoring. There were varying degrees of separation in the lead-location thresholds. These values did not appear to be consistent across level or diagnosis. A smaller degree of separation between sensory and motor thresholds during awake testing held true in the asleep patient for SSEP and f-EMG thresholds. This was further confirmed with post-operative programming demonstrating the accuracy of neuromonitoring for placement. Impedances did not appear to alter the separation in thresholds or amount of stimulation required for responses. One patient was combative during the awake testing period and therefore motor thresholds were not obtained. This same patient was determined to have a ventral placement confirmed with awake and asleep neuromonitoring testing.

This disclosure demonstrates that the proposed neuromonitoring protocol can be used in an asleep patient to assure proper positioning of the DRG electrode in the dorsal foramen by generating SSEP responses in the absence of EMG responses.

Neuromonitoring was utilized by interpreting the presence of SSEP and f-EMG. SSEP was used as a marker of generated paraesthesia, while f-EMG would indicate motor contraction. Proper lead placement in the dorsal foramen was confirmed by generating SSEP responses in the absence of EMG responses. To determine proper placement, the stimulation was performed until an EMG response was activated. The stimulation was then lowered until the EMG response completely resolved and then the presence of SSEP was confirmed. This was then lowered to find its threshold. The presence of an SSEP below the EMG threshold confirmed dorsal placement. The absolute thresholds and levels of stimulation for both SSEP and EMG were considered to be of less significance. If the SSEP was not present at the EMG threshold it would prompt a repositioning of the lead secondary to a ventral placement. The data collected from each patient is included in Table 3.

TABLE 3

Response Thresholds with Stimulation

| Patient | Lead Location-Threshold | Awake (mAmps) | Neuro-monitoring (mAmps) | Post-Operative Program (mAmps) | Impedance Intra-Op (Ohms) |
|---|---|---|---|---|---|
| A | Left L5-Sensory | 1.2 | 1.2 | 1.23 | 3137 |
|   | Left L5-Motor | 3.3 | 3.3 | 1.8 |  |
| B | Left L3-Sensory | 1.18 | 1.3 | 0.4 | 1665 |
|   | Left L3-Motor | 3.5 | 1.7 | 0.8 |  |
| C | Right L1-Sensory | 0.4 | 1.6 | 2.5 | 977 |
|   | Right L1-Motor | 1.35 | 2.2 | 3.2 |  |
|   | Right L2-Sensory | 0.25 | 0.5 | 0.5 | 1351 |
|   | Right L2-Motor | 0.45 | 1.15 | 0.85 |  |
| D* | Left L4-Sensory | 0.875 | 0.5 | 1.68 | 1855 |
|   | Left L4-Motor | N/O** | 0.6 |  |  |
|   | Right L4-Sensory | 0.85 | 1.4 | 1.65 | 1118 |
|   | Right L4-Motor | N/O** | 1.7 |  |  |
|   | Left L5-Sensory | 1.5 | 1.3 | 0.45 | 2209 |
|   | Left L5-Motor | N/O** | 2.3 |  |  |
|   | Right L5-Sensory | 0.55 | 0.4 | 0.55 | 1491 |
|   | Right L5-Motor | N/O** | 0.9 |  |  |
| E | Left L4-Sensory | 0.5 | 0.55 | 0.7 | 2214 |
|   | Left L4-Motor | 0.75 | 0.7 | 1 |  |
|   | Left L5-Sensory | 0.5 | 1.3 | 0.7 | 2894 |
|   | Left L5-Motor | 0.75 | 1.75 | 1 |  |
| F | Left L5-Sensory | 0.4 | 0.6 | 0.4 | 1986 |
|   | Left L5-Motor | 0.8 | 1.36 | 0.8 |  |
|   | Right L5-Sensory | 0.5 | 0.25 | 0.25 | 1567 |
|   | Right L5-Motor | 0.9 | 0.31 | 0.7 |  |

*Patient did not tolerate awake testing; combative upon awakening and was difficult for assessment; awake motor thresholds not determined.
**Not obtained.

Table 3 includes sensory and motor thresholds for each patient with asleep neuromonitoring testing, sensory and motor thresholds (when able) for awake testing, as well as post-operative programming parameters. Patient D was combative during the awake testing period and therefore motor thresholds were not obtained. This same patient was determined to have a ventral placement on the first attempt at a left L4 placement. He returned with motor contractions at 0.5 mA without generation of paraesthesias. This lead was subsequently tested under neuromonitoring prior to repositioning. EMG thresholds returned at 0.4 mA without the presence of SSEP responses below this threshold.

These results confirm that the proposed protocol can be used to assure proper positioning of the DRG electrode in the dorsal foramen. Proper lead placement in the dorsal foramen was confirmed by generating SSEP responses in the absence of EMG responses. There are several benefits for the use of neuromonitoring to confirm lead placement in an asleep patient. There is an increased improved comfort of the procedure for the patient and physician, as well as a method of verification to confirm proper placement without awake intraoperative testing. Specifically, the degree of comfort to the asleep patient may be of additional interest in the placement of DRG electrodes as the brushing of the electrode across the DRG can be a painful experience in the awake patient. Awake testing in one of the patients of this series lead to incomplete testing given the patient was combative and difficult to assess which would also demonstrate one potential benefit of asleep testing. The patient remains anesthetized throughout the procedure, and the accuracy of the placement and expected sensory and motor thresholds for stimulation are determined objectively using a combination of SSEP and f-EMG testing. Other benefits of lead placement on an asleep patient are lower rates of adverse events, and less pain during the procedure.

If the SSEP was not present at the EMG threshold, it would prompt a repositioning of the lead secondary to a ventral placement. This was seen on the initial placement of a Left L4 lead in one of the patients which demonstrated motor contractions without paraesthesias during awake testing and was further confirmed by having an EMG threshold with neuromonitoring below that of the SSEP threshold. Contact configuration could also be adjusted based on responses for further clarification and testing.

One should also recognize that there was decreased cortical representation of upper lumbar levels compared to lower as evidenced by the typical depiction of the sensory homunculus. Also, the presence of scar tissue or thickened dura may inhibit a clear separation of motor and sensory thresholds or cause excessive threshold levels compared to expectations.

The terms and descriptions used herein are set forth by way of illustration only and are not meant as limitations. Those skilled in the art will recognize that many variations are possible within the spirit and scope of the invention. All modifications, variations and alterations are intended to be covered and all terms are to be understood in their broadest possible sense unless otherwise indicated.

What is claimed is:

1. A method for confirming placement of an electrode in a subject, the method comprising:
    implanting a stimulating electrode on a nerve fiber in proximity to a dorsal root ganglion;
    providing increasing amount of electrical stimulation via an external stimulator to the nerve fiber via the stimulating electrode to elicit a somatosensory evoked potential response and an electro-myogram response;
    measuring the somatosensory evoked potential response and the electro-myogram response using a plurality of recording electrodes;
    decreasing amount of electrical stimulation to the nerve fiber until there is no detectable electro-myogram response;

ensuring continued somatosensory evoked potential response; and determining correct placement of the stimulating electrode on a dorsal nerve fiber of the dorsal root ganglion when there is presence of a continued somatosensory evoked potential response in the absence of the detectable electro-myogram response.

2. The method of claim 1, further comprising the steps of:

determining incorrect placement of the stimulating electrode on a ventral nerve fiber of the dorsal root ganglion when there is no continued somatosensory evoked potential response in the absence of the detectable electro-myogram response; and repositioning the stimulating electrode on the nerve fiber of the dorsal root ganglion.

3. The method of claim 1, wherein the subject is unable to provide verbal feedback.

4. The method of claim 1, wherein the stimulating electrode is supplied with electrical stimulation from a neuromonitoring device using an adaptor.

5. The method of claim 1, wherein the step of implanting a stimulating electrode on the nerve fiber of the dorsal root ganglion is guided by fluoroscopic imaging.

6. The method of claim 1, wherein the electro-myogram response is measured using a recording electrode placed at a muscle group corresponding to a dermatomal level ranging throughout a spine.

7. The method of claim 6, wherein the dermatomal level can include one or more of a cervical, thoracic, or lumbar level.

8. The method of claim 1, wherein the electro-myogram response is measured using a recording electrode placed in an adductor hallucis muscle and the stimulating electrode in a L5 dermatome.

9. The method of claim 1, wherein the electro-myogram response is measured using a recording electrode placed in an iliopsoas muscle and the stimulating electrode in a L1 dermatome.

10. The method of claim 1, wherein the electro-myogram response is measured using a recording electrode placed in an adductor brevis or longus muscle and the stimulating electrode in a L2 dermatome.

11. The method of claim 1, wherein the electro-myogram response is measured using a recording electrode placed in a quadricep muscle and the stimulating electrode in a L3 or L4 dermatome.

12. The method of claim 1, wherein the electro-myogram response is measured using a recording electrode placed in a gastrocnemius muscle and the stimulating electrode in a S1 dermatome.

13. A system for placement of an electrode in a subject, the system comprising:

a stimulating electrode operable to be implanted in proximity to a nerve fiber of a dorsal root ganglion; and a neuromonitoring device electronically coupled to the stimulating electrode, wherein the neuromonitoring device comprises circuitry that is operable to:

provide an increasing amount of electrical stimulation to the nerve fiber via the stimulating electrode to elicit a somatosensory evoked potential response and an electro-myogram response;

measure the somatosensory evoked potential response and the electro-myogram response using a plurality of recording electrodes;

decrease an amount of electrical stimulation to the nerve fiber until there is no detectable electro-myogram response;

ensure continued somatosensory evoked potential response; and determine correct placement of the stimulating electrode relative to the dorsal root ganglion when there is presence of a continued somatosensory evoked potential response in the absence of the detectable electro-myogram response.

14. The system of claim 13, wherein the subject is unable to provide verbal feedback.

15. The system of claim 13, wherein the stimulating electrode is supplied with electrical stimulation from a neuromonitoring device using an adaptor.

16. The system of claim 13, further comprising fluoroscopic imaging to support the implanting of the stimulating electrode.

17. The system of claim 13, wherein the electro-myogram response is measured using a recording electrode placed at a muscle group corresponding to a dermatomal level ranging throughout a spine.

18. The system of claim 17, wherein the dermatomal level can include one or more of a cervical, thoracic, or lumbar level.

19. The system of claim 13, wherein the electro-myogram response is measured using a recording electrode placed in an adductor hallucis muscle and the stimulating electrode in a L5 dermatome.

20. The system of claim 13, wherein the electro-myogram response is measured using a recording electrode placed in an iliopsoas muscle and the stimulating electrode in a L1 dermatome.

21. The system of claim 13, wherein the electro-myogram response is measured using a recording electrode placed in an adductor brevis or longus muscle and the stimulating electrode in a L2 dermatome.

22. The system of claim 13, wherein the electro-myogram response is measured using a recording electrode placed in a quadricep muscle and the stimulating electrode in a L3 or L4 dermatome.

23. The system of claim 13, wherein the electro-myogram response is measured using a recording electrode placed in a gastrocnemius muscle and the stimulating electrode in a S1 dermatome.

* * * * *